(12) United States Patent
Hochstrasser et al.

(10) Patent No.: US 7,438,861 B2
(45) Date of Patent: Oct. 21, 2008

(54) HEATABLE PIPETTE

(75) Inventors: Remo Anton Hochstrasser, Oberwil (CH); Dieter Voegelin, Sissach (CH); Frédéric Ran, Kembs (FR)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 11/804,279

(22) Filed: May 16, 2007

(65) Prior Publication Data
US 2007/0274870 A1 Nov. 29, 2007

(30) Foreign Application Priority Data
May 23, 2006 (EP) .................................. 06405221

(51) Int. Cl.
*B01L 3/02* (2006.01)
(52) U.S. Cl. ...................................................... 422/100
(58) Field of Classification Search .................. 422/100
See application file for complete search history.

(56) References Cited

U.S. PATENT DOCUMENTS 6,260,407 B1    7/2001   Petro et al.

FOREIGN PATENT DOCUMENTS

| DE | 38 38 626 A1 | 5/1990 |
|---|---|---|
| DE | 39 21 393 A1 | 1/1991 |
| DE | 44 23 267 A1 | 1/1996 |
| EP | 1 134 024 B1 | 9/2001 |
| EP | 1 206 969 B1 | 5/2002 |
| WO | WO 98/57180 | 12/1998 |
| WO | WO 00/45955 A | 8/2000 |
| WO | WO 03/014732 A1 | 2/2003 |

OTHER PUBLICATIONS

European Search Report No. EP 06405221.0, date of completion of search Aug. 23, 2006.

*Primary Examiner*—Walter D. Griffin
*Assistant Examiner*—Bobby Ramdhanie
(74) *Attorney, Agent, or Firm*—Mintz, Levin, Cohn, Ferris, Glovsky & Popeo

(57) ABSTRACT

A heatable pipette, with a needle has an inner channel defined by an inner wall, arranged to conduct electric current through the inner wall for resistively heating the inner wall. The needle has an outer wall, which is defined between the outer wall and the inner wall and connectable for providing pressure air into the outer channel. By conducting current directly through the inner wall, the inner wall itself operates as resistor. Particularly, if the inner wall is made of an appropriate material, for example of stainless steel, the ohmic resistance of the inner wall is not negligible even if the inner wall is very thin. Therefore, the inner wall can directly be used as resistor for resistance heating of the inner wall even if the needle is manufactured in small dimensions.

8 Claims, 1 Drawing Sheet

HEATABLE PIPETTE

TECHNICAL FIELD

The present invention relates to a heatable pipette, in general, and more particularly to a heatable pipette with a needle having an inner channel defined by an inner wall for conducting electric current.

BACKGROUND ART

In various chemical, biochemical or pharmaceutical applications local transfer of fluids is involved. A common way for such transfer is by means of a pipette wherein the fluid can be retrieved into the pipette via a needle, the pipette can be relocated and then the fluid can be dispensed at a final location out of the pipette. Often, the fluids to transfer need to be kept in a certain temperature range which can be achieved by heating the needle of the pipette.

For example, many processes for creating certain chemical compounds involve solutions comprising a solute dissolved in a solvent. In order to be able to dissolve a favourable amount of solute, the solution is often equilibrated at an elevated temperature close to the boiling point of the solvent. In order to prevent crystal formation or precipitation caused by cooling, such solutions can be transferred using a heatable pipette.

As an example of an according heatable pipette, WO 03/014732 A1 discloses a pipette system comprising a needle for dispensing or retrieving a liquid and a heat sink for maintaining a specific temperature of the liquid. The heat sink encloses a section of the needle in order to be capable of transmitting heat to the needle. Since only a section of the needle is heated by means of the heat sink, the temperature of the liquid inside the needle decreases with increasing distance to the heat sink. Particularly, if needles are used having a large section not being enclosed by the heat sink, said decrease of temperature can cause crystal formation or precipitation to a certain extent.

In U.S. Pat. No. 6,260,407 B1 a pipette is shown comprising a double walled needle. Between the two walls a temperature control element is arranged being capable of heating more or less the entire length of the needle. Said element can for example be arranged as a resistive wire being wound between the two walls of the needle or as an according fluid containing tubular coil. Such arrangements are usually not efficiently feasible in small dimension.

Therefore there is a need for a heatable pipette with a needle, being capable of heating more or less the entire length of the needle and being simply producible in comparably small dimensions.

DISCLOSURE OF THE INVENTION

According to the invention, the need for a heatable pipette with a needle, being capable of heating more or less the entire length of the needle and being simply producible in comparably small dimensions is settled by a heatable pipette as it is defined by the features below.

In particular, the invention deals with a heatable pipette with a needle having an inner channel defined by an inner wall. The pipette is arranged to conduct an electric current through the inner wall for resistively heating the inner wall wherein, preferably, the electric current is conducted in an essentially longitudinal direction through the inner wall. The needle has an outer wall wherein an outer channel is defined between the outer wall and the inner wall. The outer channel is connectable to pressure air means for providing pressure air into the outer channel and the outer channel has outlet openings for providing the pressure air out of the outer channel.

By conducting current directly through the inner wall, the inner wall operates as resistor. Particularly, if the inner wall is made of an appropriate material, for example of stainless steel, the ohmic resistance of the inner wall is not negligible. Therefore, the inner wall can directly be used as resistor for resistance heating of the inner wall even if a needle in comparably small dimensions is used.

The temperature of the inner wall correlates to the voltage and the amperage applied to the inner wall. Therefore, it can easily be adjusted on a fine scale by regulating the properties of the current. Further, since the current is conducted in an essentially longitudinal direction of the needle, the inner wall can be heated over more or less its entire length. Thus, a fluid being inside the inner channel can be kept on an exact predefined temperature.

The outer channel and the outer wall can be used for various purposes in various applications of the pipette. In particular, the use of pressure air can be a need in various applications of the pipette. For example, when used in a filtration device the needle of the pipette can be arranged through a septum into a filter chamber. The filter chamber is for example connected to a collecting chamber via a filter element. Since the septum seals the needle inside the filter chamber, the pressure air provided into the filter chamber via the outlet openings effects an overpressure inside the filter chamber. This overpressure can drive a fluid provided into the filter chamber by the needle through the filter element into the collecting chamber.

In a preferred embodiment a conductive connection between the outer wall and the inner wall is arranged at a distal end region of the pipette and the pipette is arranged to conduct electric current through the inner wall and the outer wall via the conductive connection. The conductive connection can for example be realized by welding.

With such an arrangement of the pipette the current can be supplied to the inner wall at a proximal end region of the pipette and be lead away from the outer wall at the proximal end region of the pipette, thereby establishing a current circuit. Thus, no current conduction means have to be arranged at the distal end region of the pipette impairing the dimensioning of the needle.

Preferably, a first electric pole is arranged at a proximal end region of the pipette contacting the inner wall and a second electric pole is arranged at the proximal end region of the pipette contacting the outer wall wherein the first electric pole is antipodal to the second electric pole. Such contacting includes direct contacting as well as indirect contacting, e.g. via another member of the pipette. Like this, the current is conducted in one longitudinal direction through the inner wall and in the reverse direction through the outer wall.

The first electric pole can be a positive pole and the second electric pole can be a negative pole. Like this, the current is conducted beginning at the proximal end of the needle in longitudinal direction through the inner wall up to the distal end region of the needle and from there for example via the conductive connection through the outer wall in the reverse direction to the negative pole being again arranged at the proximal end region of the pipette.

Preferably, the thickness of the inner wall varies along the needle. By adapting the thickness of the inner wall in longitudinal direction of the needle the ohmic resistance of the inner wall can be adapted by sectors such that the gradient of temperature along the needle can be optimized. Thus, the temperature conditions of a fluid being inside the inner channel can be optimized and an improved homogeneous temperature of the fluid can be achieved.

The outlet openings can be arranged at a distal end region of the pipette and the outer channel is connected to the pressure air means at a proximal end region of the pipette. Frequently, the pressure air is needed more or less at the same location as the fluid is supplied. Therefore, the outlet openings are preferably arranged near the supply opening of the inner channel.

Preferably, a temperature sensor is arranged to detect the temperature of the inner wall. The temperature sensor allows the temperature of the inner wall to be controlled and according adjustments of the current to be performed for stabilizing the temperature. It can for example be connected to automatic control means for adjusting the current being conducted through the inner wall wherein the control means can react on changes of the temperature.

In a preferred embodiment the outer wall passes into a housing at the proximal end region of the pipette, the housing having a pressure air connection being connected to the pressure air means such that pressure air is providable into the outer channel via the housing. The temperature sensor is arranged inside the housing and a sealing is arranged inside the housing between the pressure air connection and the temperature sensor for protecting the sensor of the pressure air. Such an arrangement is a convenient realization of the pipette according to the invention. Since most of the equipment for proving, adjusting and controlling the temperature and the pressure air is arranged at the proximal end region of the pipette, the needle can be comparably small dimensioned.

BRIEF DESCRIPTION OF THE DRAWINGS

The heatable pipette according to the invention is described in more detail hereinbelow by way of an exemplary embodiment and with reference to the attached drawing, wherein.

BEST MODE(S) FOR CARRYING OUT THE INVENTION

Figure 1:
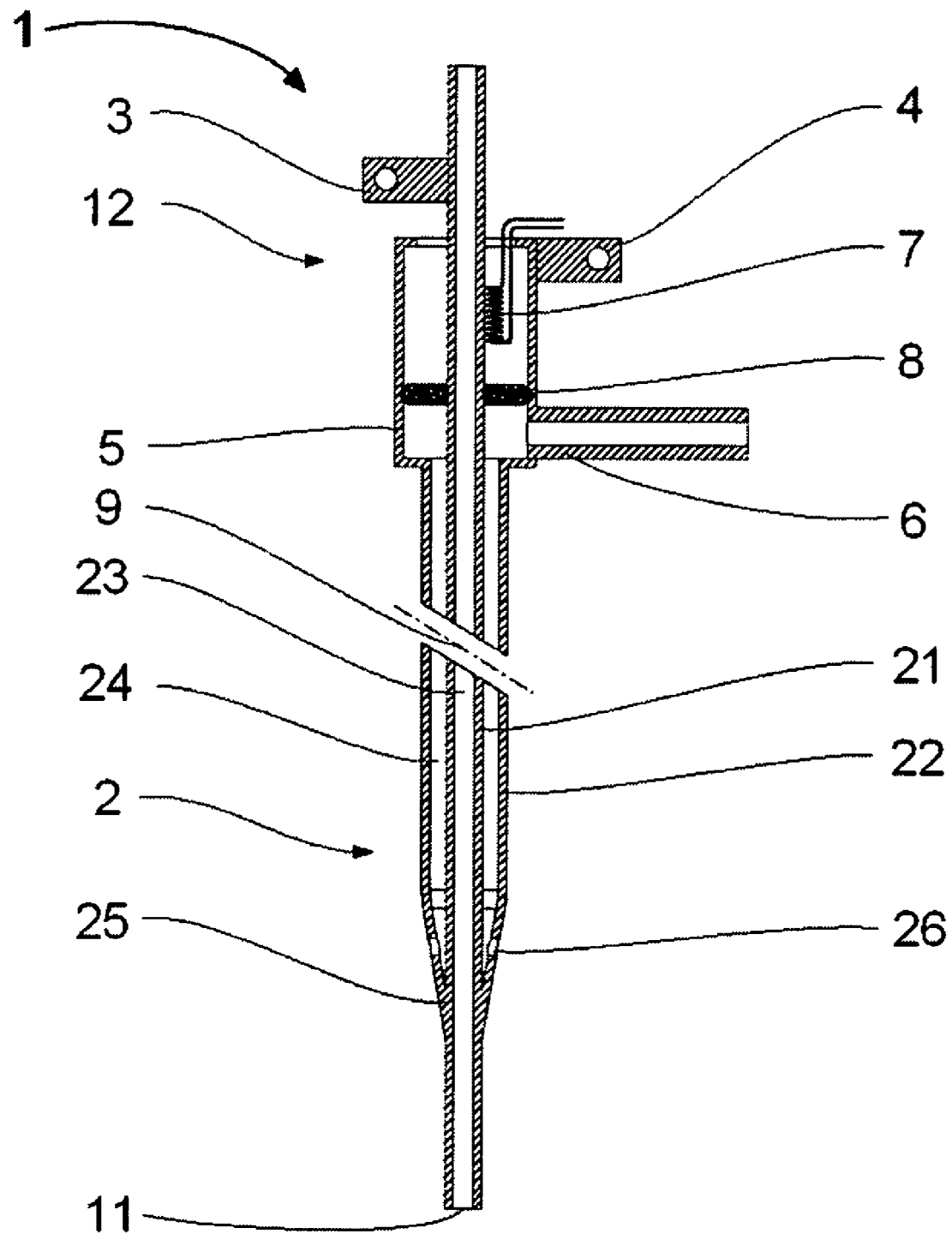
FIG. 1 shows a cross section view of the heatable pipette according to the present invention.

The cross section of the FIG. 1 shows a heatable pipette 1 according to the invention wherein for better illustration of the essential parts it is separated in two portions as indicated by dotted line 9.

The heatable pipette 1 has a double walled needle 2 comprising an inner channel 23 defined by an inner wall 21 and an outer channel 24 being arranged between the inner wall 21 and a concentric outer wall 22. The inner wall 21 as well as the outer wall 22 have circular cross sections (not visible in the FIG. 1) such that the inner channel 23 has the shape of a circular tube and the outer channel 24 has the shape a annular tube. The inner wall 21 is connected to the outer wall 22 by a conductive connection 25 being arranged near a distal end 11 of the heatable pipette 1. At the end of the outer channel 24 near the distal end 11 of the heatable pipette 1 outlet openings 26 are arranged in the outer wall 22.

At a proximal end region 12 of the heatable pipette 1 the outer wall 22 passes into a housing 5. The inner channel 23 extends through and beyond the housing 5. Near the end of the housing 5 close to the outer wall 22 a pressure air connection 6 is arranged connecting the housing 5 with pressure air means such as for example a pump (not shown in the FIG. 1). Adjacent to the pressure air connection 6 an annular sealing 8 is arranged inside the housing 5 and around the inner channel 23. Above the sealing 8 a temperature sensor 7 is arranged inside the housing 5 being in contact with the inner wall 21. At the inner channel 23 above the housing 5 a positive pole 3 is arranged being in contact with the inner wall 21 and at the housing 5 a negative pole 4 is arranged being in contact with the outer wall 22 via the housing 5.

In use, positive pole 3 provides a current to the inner wall 21. The current is conducted in longitudinal direction through the inner wall 21, through the conductive connection 25, through the outer wall 22 and through the housing 5 to the negative pole 4. The inner wall 21, the conductive connection 25, the outer wall 22 and the housing 5 are resistors in the circuit generated by the positive pole 3 and the negative pole 4 wherein particularly the resistance of the inner wall 21 is used to heat the inner wall 21. The generated heat of the inner wall 21 is then transferred to a fluid being supplied or retrieved through the inner channel 23. Thus, the temperature of the fluid can be kept in a predefined range, thereby for example preventing precipitation, crystal formation or the like by cooling of the fluid. The inner wall 21 is made of stainless steel such that the resistance of the inner wall 21 is sufficient for heating the fluid to an accurate temperature while the inner wall 21 is comparably thin.

As known by a person skilled in the art, current circuits as described above can precisely be controlled and adjusted. Thus, the temperature of the inner wall 21 is as well exactly adjustable such that the temperature of the fluid can be kept in a narrow predefined range. Since overheating the fluid and thereby for instance boiling the fluid can also adversely affect the application of pipette 1, such exact adjustment allows to keep the fluid on a maximum possible temperature without overheating it.

The temperature of the inner wall 21 is measured by temperature sensor 7. This measurement can be used to control and adjust the current as described above. For evaluating the measured temperature and accordingly adjusting the current, an automated control unit as it is known in the art can be connected to the temperature sensor 7 and the positive pole 3. Thus, a predefined temperature depending on the properties of the fluid can be set in the control unit by a user, which is the automatically controlled and adjusted.

Through the pressure air connection 6 pressure air can be provided through the housing 5 and the outer channel 24 out of the outlet openings 26. Such pressure air provision near the distal end 11 of the heatable pipette 1 can be of use in various applications of the heatable pipette 1. For example, when used in a multi-well filtration device for filtering suspensions, which comprises a filtration chamber and a collecting well being separated from each other by a filter element, the pressure air can be used to produce overpressure inside the filtration chamber and thereby driving the suspension through the filter element into the collecting well. For this purpose, the heatable pipette 1 has to be arranged sealed inside the filtration chamber when the overpressure is to apply. This can for example be achieved by a septum covering the filtration chamber and being penetrated by the needle 2 of the heatable pipette 1. Further for the use in such a multi-well filtration device, the heatable pipette 1 can additionally comprise a longitudinal groove for pressure equalisation being in connection with the collecting well and the outside of the multi-well filtration device. Such a groove allows pressure equalisation passing the septum without impairing the provision of overpressure inside the filtration chamber.

For protecting the temperature sensor 7 of the overpressure air or of gases, the sealing 8 seals the housing 5 between the pressure air connection 6 and the temperature sensor 7.

Other alternative embodiments of the heatable pipette according to the invention are conceivable. Explicitly mentioned in this context are:

- The pipette can also be arranged with a single walled needle wherein the current circuit can be conducted in an other way than via an outer wall.
- For achieving an as homogenous temperature in the fluid as possible, the resistance of the inner wall can be varied along the inner channel by varying the thickness of the inner wall.

What is claimed is:

1. A heatable pipette with a needle having an inner channel defined by an inner wall, wherein:
   - the pipette is arranged to conduct electric current through the inner wall for resistively heating the inner wall,
   - the needle has an outer wall, and
   - an outer channel is defined between the outer wall and the inner wall, wherein the outer channel is connectable to pressure air means for providing pressure air into the outer channel and wherein outlet openings are arranged in the outer wall so as to allow pressure air to be provided through the outer channel out of the outlet openings.

2. The heatable pipette of claim 1, wherein a conductive connection between the outer wall and the inner wall is arranged at a distal end region of the pipette and the pipette is arranged to conduct electric current through the inner wall and the outer wall via the conductive connection.

3. The heatable pipette of claim 1, wherein a first electric pole is arranged at a proximal end region of the pipette contacting the inner wall and a second electric pole is arranged at the proximal end region of the pipette contacting the outer wall wherein the first electric pole is antipodal to the second electric pole.

4. The heatable pipette of claim 3, wherein the first electric pole is a positive pole and the second electric pole is a negative pole.

5. The heatable pipette of claim 1, wherein the thickness of the inner wall varies along the needle.

6. The heatable pipette of claim 1, wherein the outlet openings are arranged at a distal end region of the pipette and the outer channel is connected to the pressure air means at a proximal end region of the pipette.

7. The heatable pipette of claim 6, wherein a temperature sensor is arranged to detect the temperature of the inner wall.

8. The heatable pipette of claim 7, wherein the outer wall passes into a housing at the proximal end region of the pipette, the housing having a pressure air connection being connected to the pressure air means such that pressure air is providable into the outer channel via the housing,
   - wherein the temperature sensor is arranged inside the housing, and
   - wherein a sealing is arranged inside the housing between the pressure air connection and the temperature sensor.

\* \* \* \* \*